United States Patent [19]

Steckel

[11] Patent Number: 5,242,608
[45] Date of Patent: Sep. 7, 1993

[54] PROCESS FOR OVERBASING VIA METAL BORATE FORMATION

[75] Inventor: Thomas F. Steckel, Chagrin Falls, Ohio

[73] Assignee: The Lubrizol Corporation, Wickliffe, Ohio

[21] Appl. No.: 740,399

[22] Filed: Aug. 5, 1991

Related U.S. Application Data

[63] Continuation of Ser. No. 564,669, Aug. 7, 1990, Pat. No. 5,064,545, which is a continuation of Ser. No. 943,297, Dec. 17, 1986, abandoned.

[51] Int. Cl.$^5$ ............... C10M 137/00; C10M 139/00
[52] U.S. Cl. ................... 252/32.5; 252/33.4; 252/32.7 E; 252/35; 252/18; 252/49.6
[58] Field of Search ............ 252/49.6, 33.4, 32.7 HC, 252/32.7 E, 32.5, 35, 18

[56] References Cited

U.S. PATENT DOCUMENTS

| | | | |
|---|---|---|---|
| 2,607,735 | 8/1952 | Sproule et al. | 252/40.5 |
| 2,614,985 | 10/1952 | Cook | 252/18 |
| 2,721,180 | 10/1955 | Lawrence et al. | 252/49.6 |
| 2,795,548 | 6/1957 | Thomas et al. | 252/49.6 |
| 2,987,476 | 6/1961 | Hartley et al. | 252/18 |
| 3,251,770 | 5/1966 | Vogel | 252/32.7 |
| 3,271,310 | 9/1966 | Le Suer | 252/35 |
| 3,306,908 | 2/1967 | Le Suer | 260/326.3 |
| 3,346,493 | 10/1967 | Le Suer | 252/32.5 |
| 3,544,614 | 12/1970 | Schwartz | 260/462 |
| 3,679,584 | 7/1972 | Hellmuth | 252/33.4 |
| 3,758,407 | 9/1973 | Harting | 252/18 |
| 3,829,381 | 8/1974 | Le Suer | 252/33.4 |
| 3,842,008 | 10/1974 | Carman | 252/18 |
| 3,907,691 | 9/1975 | King et al. | 252/33.4 |
| 3,912,643 | 10/1975 | Adams | 252/49.6 |
| 3,912,644 | 10/1975 | Adams | 252/49.6 |
| 4,252,659 | 2/1981 | Ali | 252/33.4 |
| 4,263,155 | 4/1981 | Frost | 252/49.8 |
| 4,394,277 | 7/1983 | Small | 252/32.7 |
| 4,459,215 | 7/1984 | Salentini | 252/32.5 |
| 4,539,126 | 9/1985 | Blecker et al. | 252/39 |
| 4,664,822 | 5/1987 | Hunt et al. | 252/33.4 |
| 4,683,126 | 7/1987 | Inoue et al. | 252/33.4 |

FOREIGN PATENT DOCUMENTS

WO85/03504 8/1985 European Pat. Off. .
WO87/04454 7/1987 European Pat. Off. .

Primary Examiner—Jacqueline V. Howard
Attorney, Agent, or Firm—Joseph P. Fischer; Frederick D. Hunter, Sr.; James L. Cordek

[57] ABSTRACT

A process of preparing an overbased composition by the reaction of oil soluble organic acids with oxides or hydroxides of, e.g., zinc, copper, cadmium, transition metals, etc. to form a salt. Additional oxides or hydroxides are added along with boric acid and promoters. These overbased metal borates are useful in lubricating oils and fuels.

25 Claims, No Drawings

PROCESS FOR OVERBASING VIA METAL BORATE FORMATION

This is a continuation of copending application(s) Ser. No. 07/564,669 filed on Aug. 7, 1990 now U.S. Pat. No. 5,064,545 which is a continuation of Ser. No. 06/943,297 filed on Dec. 17, 1986, abandoned.

BACKGROUND OF THE INVENTION

This invention relates to the preparation of oil-soluble, metal-containing compositions and to the use of such compositions in lubricants and fuels. More particularly, this invention relates to the metal overbasing of organic acids by the use of a boron compound.

Conventional overbasing uses acidic gases, such as $CO_2$, $SO_2$ and $H_2S$ with $CO_2$ being the most preferred inorganic acidic material. This is due to overall considerations of cost, ease of use, availability and performance of the resulting products. This type of overbasing wherein M is a metal occurs in the following manner: An excess amount of a metal hydroxide is reacted with an acid. This acid reacts with a stoichiometric amount of the metal hydroxide to form a metal salt. $CO_2$ is introduced into the reaction system, and the $CO_2$ immediately reacts with the metal hydroxide to form a metal carbonate. The presence of the large amount of metal carbonate in the reaction system is evidence of overbasing.

This invention deals with the formation of an overbased product formed by the reaction of zinc oxide, zinc hydroxide, copper oxide or copper hydroxide with an organic acid to form the salt. Additional zinc oxide or copper hydroxide is added along with boric acid to form a zinc or copper borate overbased acid.

DESCRIPTION OF THE RELATED ART

U.S. Pat. No. 3,629,109 (Gergel et al, Dec. 21, 1971) discusses the preparation of basic magnesium salts of organic acids by the reaction of an inorganic acidic material, such as $CO_2$ with alkali or alkaline earth metal salts in the presence of a promoter system.

U.S. Pat. No. 3,829,381 (Le Suer, Aug. 13, 1974) deals with post-treating a calcium overbased, petroleum sulfonic acid with boric acid to obtain a boron and a calcium-containing reaction product. This composition is useful as an additive in lubricants and fuels.

SUMMARY OF THE INVENTION

This invention is directed towards basic oil-soluble metal salts of organic acids, processes for preparing such basic salts and to lubricating compositions containing these basic salts. More particularly, the invention is concerned with basic zinc, copper, cadmium or transitional metal salts of organic acids prepared by a process which comprises contacting an oil-soluble acidic compound such as a sulfonic acid, a carboxylic acid, a substituted phenol, a phosphorus acid or mixtures thereof with a metal-containing compound such as oxides or hydroxides of zinc or copper to form a metal salt. This metal salt is further reacted with boric acid and additional metal compound in the presence of a promoter system.

DETAILED DESCRIPTION OF THE INVENTION

The metal-containing borate overbased compositions of the present invention may be prepared by reacting (A) a source of an oil-soluble organic acid with (B) a metal-containing compound, (C) and a boron compound in the the presence of (D) a promoter system.

The invention further provides for additive concentrates and lubricant compositions comprising compositions formed by the above process.

Component (A)

Component (A) is a source of an oil-soluble organic acid. These organic acids are sulfonic acids, carboxylic acids, phosphorus acids or mixtures thereof.

Suitable carboxylic acids are of the formula $R(COOH)_n$ wherein n is an integer of at least one and R is a hydrocarbyl based group. Suitable carboxylic acids include aliphatic, cycloaliphatic and mono- and polybasic carboxylic acids, such as the naphthenic acids, alkyl or alkenyl substituted cyclopentanoic acids, alkyl or alkenyl substituted cyclohexanoic acids. R generally contains at least 8 carbon atoms, and preferably at least 12 carbon atoms. Generally, if the aliphatic carbon chain is branched, the acids are more oil soluble for any given carbon atom content. The cycloaliphatic and aliphatic carboxylic acids can be saturated or unsaturated. Specific examples include 2-ethylhexanoic acid, linolenic acid, propylene tetramer substituted maleic acid, behenic acid, isosteric acid, pelargonic acid, capric acid, palmitoleic acid, linoleic acid, lauric acid, oleic acid, ricinoleic acid, undecylic acid, dioctylcyclopentane carboxylic acid, myristic acid, commercially available mixtures of two or more carboxylic acids, such as tall oil acids, rosin acids and the like.

Carboxylic acids of the formula:

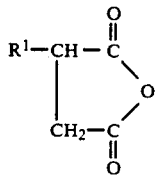

wherein the organic acid is a hydrocarbyl substituted succinic anhydride is also suitable as Component (A) in this invention. The hydrocarbyl substituted succinic anhydride used in the practice of this invention is well known to those of skill in the art and have been found to be useful as additives for lubricants and fuels and as intermediates for preparing the same. See for example the following U.S. Pat. Nos. which are hereby incorporated by reference for their disclosure relating to the preparation of carboxylic acid acylating agents: 3,219,666; 3,272,746; 3,381,022; 3,254,025; 3,278,550; 3,288,714; 3,271,310; 3,373,11; 3,346,354; 3,272,743; 3,374,174; 3,307,928; and 3,394,179.

Generally, the hydrocarbyl substituted succinic anhydride is prepared by reacting an olefin polymer or chlorinated analog thereof with an unsaturated carboxylic acid or derivative thereof such as acrylic acid, fumaric acid, maleic anhydride and the like.

The hydrocarbyl substituted succinic anhydride has at least one hydrocarbyl-based substituent $R^1$ of about 20 to about 500 carbon atoms. Generally, this substitutent has an average of at least about 30, and often at least about 50 carbon atoms. Typically, this substituent has a maximum average of about 300, and often about 200 carbon atoms. As used herein, the term "hydrocarbon-based", hydrocarbon-based substituent" and the like denotes the substituent having a carbon atom directly attached to the remainder of the molecule (i.e., the carboxylic acylating portion and having predominantly hydrocarbyl character within the context of this invention. Such substituents include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents may together form an alicyclic radical);

(2) substituted hydrocarbon substituents, that is, those substituents containing non-hydrocarbon radicals which, in the context of this invention, do not alter the predominantly hydrocarbyl substituent; those skilled in the art will be aware of such radicals (e.g., halo (especially chloro and fluoro), alkoxyl, hydroxyl, mercapto, alkylmercapto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of skill in the art and include, for example, sulfur, oxygen, nitrogen and such substituents as e.g., pyridyl, furanyl, thiophenyl, imidazoly, etc., are exemplary of these hetero substituents.

In general, no more than about three radicals or heteroatoms and preferably no more than one, will be present for each ten carbon atoms in the hydrocarbon-based substituents. Typically, there will be no such radicals or heteroatoms in the hydrocarbon-based substituents and it will, therefore, be purely hydrocarbyl.

In general, the hydrocarbon-based substituents of at least about 20 carbon atoms present in the succinic anhydride used in this invention are free from acetylenic unsaturation; ethylenic unsaturation, when present will generally be such that there is no more than one ethylenic linkage present for every ten carbon-to-carbon bonds in the substituent. The substituents are often completely saturated and therefore contain no ethylenic unsaturation.

As noted above, the hydrocarbon-based substituents present in the succinic anhydride of this invention are derived from olefin polymers or chlorinated analogs thereof. The olefin monomers from which the olefin polymers are derived are polymerizable olefins and monomers characterized by having one or more ethylenic unsaturated group. They can be monoolefinic monomers such as ethylene, propylene, butene-1, isobutene and octene-1 or polyolefinic monomers (usually di-olefinic monomers such as butadiene-1,3 and isoprene). Usually these monomers are terminal olefins, that is, olefins characterized by the presence of the group

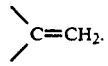

However, certain internal olefins can also serve as monomers (these are sometimes referred to as medial olefins). When such medial olefin monomers are used, they normally are employed in combination with terminal olefins to produce olefin polymers which are interpolymers. Although the hydrocarbyl-based substituents may also include aromatic groups (especially phenyl groups and lower alkyl and/or lower alkoxy-substituted phenyl groups such as para(tertiary butyl)-phenyl groups) and alicyclic groups such as would be obtained from polymerizable cyclic olefins. The olefin polymers are usually free from such groups. Nevertheless, olefin polymers derived from such interpolymers of both 1,3-dienes and styrenes such as butadiene-1,3 and styrene or para(tertiary butyl)styrene are exceptions to this general rule.

Generally, the olefin polymers are homo- or interpolymers of terminal hydrocarbyl olefins of about 2 to about 16 carbons atoms. A more typical class of olefin polymers is selected from that group consisting of homo- and interpolymers of terminal olefins of two to six carbon atoms, especially those of two to four carbon atoms.

Specific examples of terminal and medial olefin monomers which can be used to prepare the olefin polymers from which the hydrocarbon-based substituents in the acylating agents used in this invention are ethylene, propylene, butene-1, butene-2, isobutene, pentene-1, hexene-1, heptene-1, octene-1, nonene-1, decene-1, pentene-2, propylene tetramer, diisobutylene, isobutylene trimer, butadiene-1,2, butadiene-1,3, pentadiene-1,2, pentadiene-1,3, isoprene, hexadiene-1,5,2-chlorobutadiene-1,3, 2-methylheptene-1, 3-cyclohexylbutene-1, 3,3-dimethylpentene-1, styrenedivinylbenzene, allyl alcohol, acrylonitrile, ethylacrylate and ethylvinylether. Of these, the purely hydrocarbyl monomers are more typical and the terminal olefin monomers are especially typical.

Often the olefin polymers are poly(isobutene)s such as obtained by polymerization of a $C_4$ refinery stream having a butene content of about 35 to about 75 percent by weight and an isobutene content of about 30 to about 60 percent by weight in the presence of a Lewis acid catalyst such as aluminum chloride or boron trifluoride. These poly(isobutene)s contain predominantly (that is, greater than 80% of the total repeat units) isobutene repeat units of the configuration

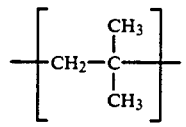

Typically, the hydrocarbyl-based substituent in the succinic anhydride as used in the present invention is an alkyl or alkenyl group of about 30, often about 50, to about 300, sometimes to about 500, carbon atoms.

Such hydrocarbyl substituted succinic anhydrides can be made by the reaction of maleic anhydride with the aforedescribed olefin polymer, as is shown in the patents referred to above. Generally, the reaction involves merely heating the two components at a temperature of about 150° to about 200°. Mixtures of these polymeric olefins, as well as mixtures of these unsaturated mono- and polycarboxylic acids can also be used.

Another source of organic acid that can be used as component (A) are the oil-soluble sulfonic acids including the synthetic oil-soluble sulfonic acids. Suitable oil-soluble sulfonic acids are are represented by the general formula $R^2SO_3H$ or $(R^2)_xArSO_3H$.

In the formulae above, $R^2$ is a hydrocarbyl based group and can be, for example, an aliphatic group such as alkyl, alkenyl, alkoxy, alkoxyalkyl, carboalkoxyalkyl, an aralkyl group, or other hydrocarbon or essentially hydrocarbon groups. X is at least one with the proviso that the variable represented by the group $(R^2)_x$ are such that the acids are oil soluble. This means that the groups represented by $(R^2)_x$ should contain at least about 8 aliphatic carbon atoms per sulfonic acid molecule, and preferably at least about 12 aliphatic carbon atoms. Generally x is an integer of 1-3. Ar is a cyclic nucleus of the mono or polynuclear type including benzenoid or heterocyclic nuclei such as a benzene, naphthalene, anthracene, 1,2,3,4-tetrahydronaphthalene, thianthrene or biphenyl nucleus and the like. Or nearly, however, Ar will represent an aromatic hydrocarbon nucleus, especially a benzene or naphthalene nucleus.

The groups Ar and $R^2$ above can also contain other substituents such as hydroxy, mercapto, halogen, nitro, amino, nitroso, carboxy, lower carboalkoxy, etc. as long as the essential hydrocarbon character of the groups is not destroyed.

Illustrative examples of the sulfonic acids are mahogany sulfonic acids, petrolatum sulfonic acids, mono-and polywax-substituted naphthalene sulfonic acids, cetylchlorobenzene sulfonic acids, cetylphenol sulfonic acids, cetylphenol disulfide sulfonic acids, cetoxycapryl benzene sulfonic acids, dicetyl thianthrene sulfonic acids, di-lauryl beta-naphthol sulfonic acids, dicapryl nitronaphthylene sulfonic acids, paraffin wax sulfonic acids, unsaturated paraffin wax sulfonic acids, hydroxy-substituted paraffin wax sulfonic acids, tetraisobutylene sulfonic acids, tetraamylene sulfonic acids, chloro-substituted paraffin wax, nitrosyl-substituted paraffin wax sulfonic acids, petroleum naphthene sulfonic acids, cetylcyclopentyl sulfonic acids, lauryl cyclohexyl sulfonic acids, mono- and polywax-substituted cyclohexyl sulfonic acids, and the like.

As used herein, the terminology "petroleum sulfonic acids" or "petrosulfonic acids" is intended to cover that well-known class of sulfonic acids derived from petroleum products according to conventional processes such as disclosed in U.S. Pat. Nos. 2,480,638; 2,483,800; 2,717,265; 2,726,261; 2,794,829; 2,832,801; 3,225,086; 3,337,613; 3,351,655; and the like. Sulfonic acids falling within the above formulae are discussed in prior U.S. Pat. Nos. as 2,616,904; 2,616,905; 2,723,234; 2,723,235, 2,723,236; 2,777,874; and the other U.S. patents referred to in each of these patents. Thus it is seen that these oil-soluble sulfonic acids are well known in the art and require no further discussion herein.

Another preferred class of organic acids suitable as component (A) are the substituted phenols of the formula:

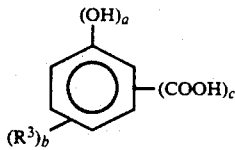

In the above formula $R^3$ is a substantially saturated hydrocarbon based group containing at least 15 carbon atoms, a and b are from 1 to 2, and c is 0 or 1. However, when b is 2, the total number of carbon atoms of $R^3$ is at least 15. Within this group of oil-soluble carboxylic acids are the aliphatic hydrocarbon-substituted salicyclic acids wherein the aliphatic hydrocarbon substituent contains an average of at least about 15 carbon atoms per ring and 1,2 or 3 substituents per molecule are particularly useful. Boron overbased products prepared from such salicyclic acids wherein the aliphatic hydrocarbon substituents are derived from polymerized olefins, particularly polymerized lower 1-mono olefins such as polyethylene, polypropylene, polyisobutylene, ethylene polypropylene, copolymers and the like having an average molecular weight of about 200 to about 1200, preferably about 300 to about 700, are very useful as lubricant additives.

The oil-soluble salicyclic acids corresponding to the above formula are well known or can be prepared according to procedures known in the art. Salicyclic acids of the type illustrated by the above formula and processes for preparing their metal salts are disclosed in such U.S. Pat. Nos. as 2,197,832, 2,197,835, 2,252,622, 2,252,664 and 2,714,092. The salts can be converted to the acids by neutralization with an inorganic acid such as HCl.

A further substituted phenol suitable as component (A) is a phenol of the formula:

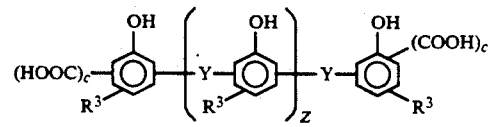

wherein $R_3$ is a substantially saturated hydrocarbyl based group containing from 6 to 100 carbon atoms, c is 0 or 1, Y is a sulfur linkage or $-CH_2-$ or mixtures thereof and Z is 0 to 30 and preferably 0 to 10. The aromatic moiety Ar is as defined above as well as being a polynuclear aromatic moiety. Such polynuclear moieties can be of the fused type, that is, wherein at least two aromatic nuclei are fused at two points to another nucleus such as found in naphthalene, anthrasene, the asanaphthalenes, etc. Such polynuclear aromatic moieties also can be of the linked type wherein at least two nuclei (either mono or polynuclear) are linked through bridging linkages to each other. Such bridging linkages can be chosen from the group consisting of carbon-carbon single bonds, ether linkages, keto linkages, sulfide linkages, polysulfide linkages of 2 to 6 sulfur atoms, sulfinyl linkages, sulfonyl linkages, methylene linkages, alkaline linkages, di-(lower alkyl) methylene linkages, lower alkaline ether linkages, alkylene keto linkages, lower alkaline sulfur linkages, lower alkaline polysulfide linkages of 2 to 6 carbon atoms, amino linkages, polyamino linkages, and mixtures of such divalent bridging linkages. In certain instances more than one bridging linkage can be present in Ar between aromatic nuclei. For example, a fluorene nucleus has two benzene nuclei linked by both a methylene linkage and a covalent bond. Such a nucleus may be considered to have 3 nuclei, but only 2 of them are aromatic. Normally Ar will contain only carbon atoms in the aromatic nuclei perse.

Another preferred class of organic acids suitable as component (A) are the phosphorus acids. These are prepared in most instances from polyisobutylene, although they may be prepared from any substantially aliphatic polymer. Thus, the polymer may be a polyethylene, polypropylene, polyhexene, polydodecene, or a polymer of other 1-mono-olefins having as many as 30 carbon atoms. It may likewise be an interpolymer in which the preponderant proportion of monomeric units is derived either from ethylene, propylene, isobutylene, or any other 1-mono-olefin having up to 30 carbon atoms. Such interpolymers are illustrated by an interpolymer of 95 molar parts of isobutylene and 5 molar parts of styrene.

In general those interpolymers are preferred in which at least 80%, on a molar basis of the interpolymer composition is derived from the aliphatic 1-mono-olefin. Such preferred interpolymers may include up to about 20%, on a molar basis, of units derived from isoprene, butadiene, piperylene, vinyl cyclohexene, chloroprene, vinyl chloride, styrene, vinyl acetate, chlorostyrene, or a vinyl alkyl ether.

The number of carbon atoms of this lower olefin polymer may vary within a rather wide range. Thus, it may be as low as 50 carbon atoms or, on the other hand, range upward to as high as 5000 carbon atoms or, in some instances, even higher. Typically, the carbon atom range is from 50–3000 carbon atoms, preferably from 50–1000 carbon atoms, and most preferably from 50–100 carbon atoms. The various types of phosphorus acids available from these polymers are prepared by reaction of the polymers with any of several well-known phosphorizing agents, followed by reaction with a reagent having an active hydrogen atom, usually water.

Illustrative phosphorus acids include, for example, the reaction products of any of these polymers with phosphorus pentasulfide and sulfur, followed by steam treatment. Another important type of phosphorus acid is that which can be prepared by the chlorination of the polyolefin followed by reaction with phosphorus trichloride and either steam or an alkyl phenol. Another type of phosphorus acid is that which is prepared by the reaction of an aliphatic polyolefin with phosphorus and sulfur monochloride, followed by steam treatment. Still another type of phosphorus acid can be prepared by reaction of a polymer of the type described before with a phosphorus sulfide, followed by steam treatment.

A general definition of the phosphorus acids contemplated for use as Component (A) includes those prepared by reaction of a polymer of a 1-mono-olefin with a phosphorizing agent, followed by treatment of the resulting product with a hydrolyzing agent. The phosphorizing agents include phosphorus sulfides, phosphorus chlorides, thiophosphoryl chloride, phosphorus pentoxide, phosphorus, and combinations of these with sulfurizing agents such as sulfur, sulfur chloride, and sulfur monochloride. Illustrative combinations of these phosphorizing and sulfurizing agents include phosphorus pentasulfide and sulfur monochloride, phosphorus and sulfur monochloride, and phosphorus pentachloride and sulfur.

The structure of such phosphorus acids is not known and in fact it is commonly believed that an acid prepared in this fashion, viz., by reaction of a polyolefin with a phosphorizing agent followed by hydrolysis of the intermediate phosphorized product, is really a mixture, not only of two or more different acids, but a mixture perhaps of different types of acids. Thus, this mixture may contain acids having carbon-to-phosphorus bonds, or acids having carbon-to-oxygen-to-phosphorus bonds, or carbon-to-sulfur-to-phosphorus bonds. Inasmuch, however, as the structure of these phosphorus acids is not known, it is necessary to refer to them in terms of the process by which they can be prepared.

Component (B)

Component (B) is a metal-containing compound. The metal-containing compound is employed as either an oxide, hydroxide, halide, carbonate, borate or mixtures thereof. Metal-containing compounds that can be used in this invention are zinc, tin, lead, cadmium or transition metals.

The transition metals of interest are those which form borates such as copper, molybdenum, manganese, nickel, cobalt, titanium, tungsten, tantalum and iron.

Especially preferred are zinc oxide, zinc hydroxide, cadmium oxide, cadmium hydroxide, copper oxide, and copper hydroxide.

Component (C)

Component (C) in the process of this invention is at least one of boric acid, boron trioxide ($B_2O_3$), boron halides (especially boron trichloride, $BCl_3$), and esters of boric acid. Any of the various forms of boric acid may be used, including metaboric acid ($HBO_2$), orthoboric acid ($H_3BO_3$) and tetraboric acid ($H_2B_4O_7$). The esters of these acids include, for example, the methyl, ethyl and propyl esters, with the methyl esters being most readily available and therefore most often used. Boric acid, and especially orthoboric acid, is preferred for use as Component (C).

Component (D)

Component D is the promoter system, i.e., that which facilitates the incorporation of metal into the basic metal compositions. The alcohols useful as this component preferably contain up to about 30 carbon atoms. They may be monohydric or polyhydric alcohols. Specific examples of the alcohols include methanol, ethanol, isopropanol, cyclohexanol, dodecanol, decanol, behenyl alcohol, ethylene glycol, diethylene glycol, triethylene glycol, monomethylether of ethylene glycol, trimethylene glycol, hexamethylene glycol, glycerol, pentaerythritol, benzyl alcohol, penylethyl alcohol, sorbitol, nitropropanol, chloroethanol, aminoethanol, cinnamyl alcohol, allyl alcohol, and the like. Especially useful are the monohydric alcohols having up to about 10 carbon atoms and mixtures of methanol with higher monohydric alcohols.

Other chemicals having utility as a promoter with or without the alcohols above are water, ammonium hydroxide, organic acids up to 8 carbon atoms, nitric acid, sulfuric acid, hydrochloric acid, a metal complexing agent such as an alkyl salicylaldoxime, and small amounts of Group I hydroxides such as lithium hydroxide, sodium hydroxide and potassium hydroxide.

The products of this invention are formed by reacting Component (A) with a portion of Component (B) to form a neutral metal salt of an organic acid. Additional Component (B) is added along with Components (C) and (D). The contents are heated to reflux and held at reflux for several hours.

The ratio of the Components (A), (B), (C) and (D) wherein Eqs. means equivalents is determined by the equation:

$$\text{Ratio} = \frac{\text{Moles of Boron}}{\text{Eqs of (B)} - \text{Eqs of (A)} - \text{Eqs of acid in (D)} + \text{Eqs of base in (D)}}$$

The preferred ratio range is from about 0.2 to about 3.0. The most preferred ratio range is from about 0.5 to about 2.0.

For the purposes of this invention, one mole of boron is equal to the number of moles of a boron compound of component (C) times the number of borons present in that boron compound. If 3.2 moles of boric acid $HBO_3$ are used, then the moles of boron is 3.2 times 1 or 3.2. If 2 moles of tetraboric acid $H_2B_4O_7$ is used, then the moles of boron is $2 \times 4$ or 8.

For the purposes of this invention, one equivalent of a metal is equal to the molecular weight of that metal divided by the valence of the metal ion. Cadmium has an equivalent weight of 56 (112 divided by 2).

The reactions of this invention may be carried out in the presence of a substantially inert liquid solvent/diluent medium. This solvent/diluent medium desirably serves to maintain contact of the components and facilitates control of the reaction temperature. Examples of suitable solvent/diluent media include aliphatic and aromatic hydrocarbons as benzene, toluene, naphtha, mineral oil, hexane; chlorinated hydrocarbons as dichlorobenzene, and heptylchloride; ethers as methyl n-amylether, n-butylether.

As used in the specification and the appended claims, the term "substantially inert" when used to refer to solvents/diluents, and the like, is intended to mean that the solvent/diluent, etc., is sufficiently inert to chemical or physical change under the conditions in which it is used. In addition, it should not materially interfere in an adverse manner with the preparation, storage, blending and/or functioning of the compositions, additive, compound, etc., in the context of the invention's intended use. For example, small amounts of a solvent/diluent, etc., can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

As used in the specification and the appended claims, the term "solvent/diluent medium" is intended to include those solvent/diluent media in which each of the components are independently soluble or stably dispersible. The term "stably dispersible" as used in the specification and the appended claims is intended to mean a composition (e.g., a single compound, a mixture of two or more compounds, etc.) capable of being dispersed in a given medium to an extent which allows it to function in its intended manner. Thus, for example, where a composition is prepared by a reaction in an oil, it is sufficient that the components be capable of being suspended in the oil in a manner sufficient to allow the reaction to occur and the formation of the composition. Thus, the term "solvent/diluent medium" is understood and can be used in a conventional manner by those of ordinary skill in the art.

The compositions of this invention may be used as a lubricant additive. However, the compositions sometimes may be accompanied by the formation of by-products and/or excess solvent/diluent medium which may lessen its commercial appeal. Accordingly, these undesirable by-product and/or excess of undesired solvent/diluent medium can be separated from the compositions of this invention by techniques known in the art; e.g., filtration, evaporation (e.g., stripping), etc., to obtain a more desirable product. Alternatively, if the solvent/diluent medium is, for example, a lubricant base suitable for use in the lubricating compositions of this invention, the product can be left in the solvent/diluent medium and used to form the lubricating compositions as described below.

The following examples are illustrative of the processes of this invention. Unless otherwise indicated in the following examples and elsewhere in the specification and claims, all parts and percentages are by weight, and all temperatures are in degrees centigrade.

EXAMPLE 1

A mixture of 561 parts (1 equivalent) of a primary branched chain monoalkyl benzene sulfonic acid (molecular weight of 500), 100 part toluene, 122 parts isobutyl alcohol and 78 parts amyl alcohol is prepared. The contents are stirred and heated to 54° C. and added are 51 parts (1.25 equivalents) zinc oxide and 40 parts water. The temperature is slowly increased to reflux of about 98° C. and held for 2.5 hours. Volatiles are then removed at 150° C. At 28° C. added are 400 parts mineral oil, 350 parts toluene, 61 parts isobutyl alcohol and 39 parts amyl alcohol. At 50° C. are added 79 parts (1.94 equivalents) zinc oxide and 124 parts (2 equivalents) boric acid. Temperature is increased to reflux of 92° C. over 1.3 hours. A solution of 10 parts zinc chloride and 90 parts water is added and reflux is maintained for an additional 7 hours. Volatiles are removed at 150° C. and 8 torr and the contents are filtered to remove any solids. Analyses: basic neutralization number, 100; ratio: 0.85.

EXAMPLE 2

The procedure of Example 1 is followed except that 9 parts acetic acid is added at the beginning of the reaction, and the 10 grams zinc chloride is omitted. Analyses: basic neutralization number, 109; % zinc, 8.76; % boron, 2.02; ratio, 0.98.

EXAMPLE 3

A mixture of 84 parts (0.15 equivalents) of the benzene sulfonic acid employed in Example 1, 561 parts (1 equivalent) of a polyisobutene (molecular weight of 1000) substituted succinic anhydride (having a saponification number of 100) and 400 parts mineral oil is prepared. The contents are stirred and heated to 98° C., and 51 parts (1.25 equivalents) of zinc oxide are added. Volatiles are removed at 150° C. over a 5.5 hour period. At 60° C. 50 parts water is added, and at 103° C. an additional 200 parts mineral oil is added and the temperature is held at 103° C. for 4 hours. 61 parts isobutyl alcohol and 39 parts amyl alcohol is added to fluidize the mixture, and then volatiles are removed at 150° C. over 2 hours to give a clear solution. At 95° C. 350 parts toluene, 61 parts isobutyl alcohol and 39 parts amyl alcohol is added. At 60° C. are added 71 parts (1.75 equivalents) zinc oxide, 124 parts (2 moles) boric acid, 90 parts water and 20 parts concentrated ammonium hydroxide. The contents are heated to reflux of 92° C. and held for 0.5 hours. 6 parts acidic acid is added and reflux is maintained another 1.25 hours. 61 parts isobutyl alcohol and 39 parts amyl alcohol is added and reflux is maintained an additional 2.5 hours. Volatiles are removed at 155° C. and 22 torr, and the contents are filtered. Analyses: basic neutralization number, 115; % zinc, 6.41; % nitrogen, 0.03; % boron, 1.24; ratio, 0.98.

EXAMPLE 4

A mixture of 898 parts (1.6 equivalents) of the benzene sulfonic acid employed in Example 1, 240 parts toluene, 183 parts isobutyl alcohol, 117 parts amyl alcohol and 14.5 parts acetic acid is prepared. The contents are stirred and heated to 84° C. and added are 82 parts (2 equivalents) zinc oxide and 64 parts water. The temperature is increased to a reflux of 95°-98° C. for 1.5 hours. Volatiles are removed at 160° C. At 60° C. are added 640 parts mineral oil, 98 parts isobutyl alcohol, 62 parts amyl alcohol, 113 parts (2.75 equivalents) zinc oxide, 198 parts (3.2 equivalents) boric acid, 160 parts water and 32 parts concentrated ammonium hydroxide. The temperature is increased to reflux of 91° C. and held at reflux for 4.5 hours. Volatiles are removed at 160° C. and 10 torr, and the contents are filtered. Analyses: basic neutralization number, 110; % zinc, 8.01; ratio, 0.93.

EXAMPLE 5

A mixture of 561 parts (1 equivalent) of the benzene sulfonic acid employed in Example 1, 48 parts (0.25 equivalents) heptylphenol, 150 parts toluene, 122 parts isobutyl alcohol and 78 parts amyl alcohol is prepared. The contents are stirred and heated to 50° C. and added are 51 parts (1.25 equivalents) zinc oxide, 40 parts water and 9 parts acetic acid. The temperature is increased to reflux of 95°-98° C. and held for 2.5 hours at reflux. Volatiles are removed at 160° C. At 90° C. added are 400 parts mineral oil, 350 parts toluene, 61 parts isobutyl alcohol, 39 parts amyl alcohol, 71 parts (1.75 equivalents) zinc oxide, 124 parts (2 moles) boric acid and 90 parts water. The temperature is increased to reflux at 95° C. and held at reflux for 6.25 hours. Volatiles are removed at 160° C. and 17 torr, and the contents are filtered. Analyses: basic neutralization number, 100; ratio, 1.25.

EXAMPLE 6

The procedure of Example 5 is followed except that 20 parts ammonium hydroxide is added prior to the 6.25 hour reflux period. Analyses: basic neutralization number, 114; % zinc, 7.93; % boron, 2.07; % nitrogen, 0.37; ratio, 1.05.

EXAMPLE 7

The procedure of Example 5 is followed except that the second additional of zinc oxide is 30.4 parts (0.75 equivalents). The boric acid is 62 parts (1 mole) and the mineral oil is 350 parts. Analyses: basic neutralization number, 63; % boron, 0.93; % nitrogen, 0.17; ratio, 1.33.

EXAMPLE 8

A mixture of 1645 parts (1.75 equivalents) of mixed straight chain dialkyl benzene sulfonic acid and branched chain monoalkyl benzene sulfonic acid (molecular weight, 385), 147 parts (0.26 equivalents) of the alkenyl succinic anhydride of Example 3, 44 parts mineral oil, 350 parts toluene, 89 parts (2.2 equivalents) zinc oxide and 70 parts water are prepared. Contents are stirred and heated to reflux of 99° C. and held at reflux for 2 hours. Volatiles are removed at 145° C. At 70° C. are added are 525 parts toluene, 156 parts (3.8 equivalents) zinc oxide, 217 parts (3.5 moles) boric acid, 10.5 parts acetic acid and 79 parts water. The contents are heated to reflux of 95° C. and held at reflux for 2 hours. Then added are 165 parts (4 equivalents) zinc oxide, 228 parts (3.7 moles) and 35 parts concentrated ammonium hydroxide at 90° C. The temperature is increased to reflux of 95° C. and held at reflux for 5 hours. Volatiles are removed at 110° C. and 350 parts mineral oil is added. Additional volatiles are removed at 160° C. and 10 torr, and the contents are filtered. Analyses: % zinc, 10.4; % boron, 2.29; ratio, 0.85

EXAMPLE 9

Essentially the same procedure of Example 8 is followed except that the sulfonic acid employed is that which is used in Example 1. Analyses: basic neutralization number, 150; ratio, 0.94.

EXAMPLE 10

A mixture of 940 parts (1 equivalent) of the sulfonic acid employed in Example 8, 84 parts (0.15 equivalents) of the alkenyl succinic anhydride employed in Example 3, 25 parts mineral oil, 200 parts toluene, 51 parts (1.25 equivalents) zinc oxide and 40 parts water is prepared. The contents are stirred and heated to reflux of 100° C. and held at reflux for 2 hours. Volatiles are removed at 165° C. At 90° C. is added 300 parts toluene, 83 parts (2 equivalents) zinc oxide, 6 parts acetic acid, 124 parts (2 moles) boric acid and 50 parts water. The temperature is increased to reflux and held for 2 hours. Two incremental additions consisting of 93 parts (2.3 equivalents) zinc oxide, 124 parts (2 moles) boric acid and 100 parts mineral oil are added at 80° C. The temperature is increased to reflux of 93° C. and held for 2 hours in each case. Then 20 parts concentrated ammonium hydroxide is added and reflux is maintained an additional 2 hours. An additional 100 parts mineral oil is added and volatiles are removed at 175° C. and 12 torr, and the contents are filtered. Analyses: basic neutralization number, 136; ratio, 0.87.

EXAMPLE 11

A mixture of 347 parts (0.3 equivalents) of the material prepared in Example 4, 125 parts toluene, 21 parts isobutyl alcohol, 24 parts amyl alcohol, 24.1 parts (0.6 equivalents) zinc oxide and 31 parts (0.5 moles) boric acid are prepared. The contents are stirred and heated and 35 parts water is added, and the temperature is maintained at reflux of 94° C. for 5 hours. Volatiles are removed at 160° C. and 10 torr, and the contents are filtered. Analyses: basic neutralization number, 149; ratio, 0.89.

EXAMPLE 12

The procedure of Example 3 is repeated except that concentrated ammonium hydroxide is not employed. Analyses: basic neutralization number, 93; % zinc, 5.63; ratio, 1.02.

EXAMPLE 13

A mixture of 561 parts (1 equivalent) of the alkenyl succinic anhydride of Example 3, 400 parts mineral oil, 28.5 parts (0.15) paratoluene sulfonic acid, 200 parts toluene, 50 parts water and 51 parts (1.25 equivalents) zinc oxide are prepared. The contents are stirred and heated to reflux of 95° C. and held at reflux for 4.5 hours. 200 parts mineral oil is added and the volatiles are removed at 155° C. At 90° C. are added 79 parts (1.94 equivalents) zinc oxide, 6 parts acetic acid, 200 parts toluene, 122 parts isobutyl alcohol, 78 parts amyl alcohol and 124 parts (2 moles) boric acid. The temperature is increased to reflux of 95° C. and maintained at reflux for 8 hours. An additional 200 parts mineral oil is added and volatiles are removed at 150° C. and 22 torr, and the contents are filtered. Analyses: basic neutralization number, 88; % zinc, 5.18; % sulfur, 0.28; ratio, 1.02.

EXAMPLE 14

A mixture of 168 parts (0.3 equivalents) of the sulfonic acid of Example 1, 2.7 parts acetic acids, 34 parts isobutyl alcohol, 21 parts amyl alcohol, 55 parts toluene and 21 parts (0.43 equivalents) cupric hydroxide is prepared. The contents are stirred and 12 parts water is added, and the contents are then heated to reflux of 92° C. and held for 4 hours. 120 parts mineral oil is added and volatiles are removed at 153° C. At 70° C. is charged 17.5 grams, 60% solution of dodecyl salicylaldoxime, 100 parts toluene, 18 parts isobutyl alcohol, 12 parts amyl alcohol, 23 parts (.47 equivalents) cupric hydroxide, 59 parts (0.95 equivalents) boric acid and 25 parts water. The temperature is increased to reflux of 93° C. and held at reflux for 7 hours. 100 parts mineral oil is added and the volatiles are removed at 160° C. and 25 torr. 50 parts mineral oil is added, and the contents are filtered. Analyses: % copper, 5.23; % boron, 1.92; ratio, 1.86.

EXAMPLE 15

To a reaction vessel is charge 1246 parts (2 equivalents) of a sodium alkyl salicylate available from Shell Oil Company. The contents are stirred and heated to 80° C. and added is 150 parts (2.2 equivalents) zinc chloride and 150 parts water. The contents are slowly heated to 120° C. over 2.5 hours. 400 parts mineral oil is added and the volatiles are removed at 175° C., and the contents are filtered. Analyses: % zinc, 4.07; % sodium, trace.

EXAMPLE 16

A mixture of 416 parts (0.5 equivalents) of the material of Example 15, 100 parts mineral oil, 200 toluene, 46 parts isobutyl alcohol, 29 parts amyl alcohol, 41 parts (1 equivalent) zinc oxide, 62 parts boric acid and 25 parts water is prepared. Stirring and heating is begun, and 6 parts acetic acid is added. The temperature is increased to reflux of 90° C. and held at reflux for 6.5 hours. An additional 20 parts water is added and reflux is continued an additional 3 hours. Volatiles are removed at 155° C. and 12 torr, and the contents are filtered. Analyses: basic neutralization number, 125; ratio, 1.11.

As previously indicated, the oil-soluble, metal-containing compositions of this invention are useful as additives for lubricants. They are particularly useful as oxidation inhibitors, corrosion inhibitors, rust inhibitors, and extreme pressure anti-wear agents in gear and bearing lubricants. They can be employed in a variety of lubricants based on diverse oils of lubricating viscosity, including natural and synthetic lubricating and grease oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Also automatic transmission fluids, transaxle lubricants, gear lubricants, metal-working lubricants, hydraulic fluids and other lubricating oil, grease compositions and aqueous systems can also benefit from the incorporation of the subject additive.

Natural oils include animal oils and vegetable oils (e.g., castor, lard oil), liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes)]; alkylbenzenes (e.g., dodecylbenzenes, tetradecylbenzenes, dinonylbenzenes, di(2-ethylhexyl) benzenes]; polyphenyls (e.g., biphenyls, terphenyls, alkylated polyphenyls); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain an amount of the oil-soluble, metal-containing compositions of this invention sufficient to inhibit oxidation, corrosion, rust and improve extreme pressure anti-wear properties. Normally the amount employed will be about 0.05% to about 20%, preferably about 0.1% to about 10% of the total weight of the lubricating composition. This amount is exclusive of any included solvent/diluent medium. In lubricating compositions operated under extremely adverse conditions, such as lubricating compositions for marine diesel engines, the metal salts of this invention may be present in amounts of up to about 30% by weight, or more, of the total weight of the lubricating composition.

The term "minor amount" as used in the specification and appended claims is intended to mean that when a composition contains a "minor amount" of a specific material that amount is less than 50 percent by weight of the composition.

The term "major amount" as used in the specification and appended claims is intended to mean that when a composition contains a "major amount" of a specific material that amount is more than 50 percent by weight of the composition.

The invention also contemplates the use of other additives in combination with the compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with an excess of a metal neutralizing agent such as the metal oxide, hydroxide, carbonate, bicarbonate, or sulfide at a temperature about 50° C. The use of a "promoter" in the neutralization step to aid the incorporation of a large excess of metal likewise is known. Examples of compound useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenylnaphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions of this invention. The following are illustrative:

(1) Reaction products of carboxylic acids (or derivatives thereof) containing at least about 34 and preferably at least about 54 atoms with nitrogen containing compounds such as amine, organic hydroxy compounds such as phenols and alcohols, and/or basic inorganic materials. Examples of these "carboxylic dispersants" are described in British Patent 1,306,529 and in many U.S. patents including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.: 3,275,554; 3,454,555; 3,438,757 and 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | | |
|---|---|---|
| 2,459,112 | 3,442,808 | 3,591,598 |
| 2,962,442 | 3,448,047 | 3,600,372 |
| 2,984,550 | 3,545,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |

-continued

| | | |
|---|---|---|
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.: 3,329,658; 3,366,730; 3,449,250; 3,687,849; 3,519,565 and 3,702,300.

The above-noted patents are incorporated by reference herein for their disclosures of ashless dispersants.

Extreme pressure agents and corrosion- and oxidation-inhibiting agents which may be included in this invention are exemplified by chlorinated aliphatic hydrocarbons such as chlorinated wax; organic sulfides and polysulfides such as benzyl disulfide, bis(chlorobenzyl) disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl napthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 10 percent to 90 percent by weight of the composition of this invention and may contain, in addition, one or more other additives known in the art or described hereinabove.

The fuel compositions of the present invention contain a major proportion of a normally liquid fuel, usually a hydrocarbonaceous petroleum distillate fuel such as motor gasoline as defined by ASTM Specification D-439-73 and diesel fuel or fuel oil as defined by ASTM Specification D-396. Normally liquid fuel compositions comprising nonhydrocarbonaceous materials such as alcohols, ethers, organonitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more nonhydrocarbonaceous materials are also contemplated. Examples of such mixtures are combinations of gasoline and ethanol, and diesel fuel and ether. Particularly preferred is gasoline, that is, a mixture of hydrocarbons having an ASTM boiling point of about 60° C. at the 10 percent distillation point to about 205° C. at the 90 percent distillation point.

Generally, these fuel compositions contain an amount of the composition of this invention sufficient to impart friction modification and/or deposit softening properties to the fuel; usually this amount is about 0.001 to about 5 percent (based on the weight of the final composition), preferably 0.001 percent to 1.0 percent.

The fuel compositions of this invention can contain, in addition to the compositions of this invention, other additives which are well known to those of skill in the art. These can include antiknock agents such as tetraalkyl lead compounds, lead scavengers such as haloalkanes (e.g., ethylene dichloride and ethylene dibromide), deposit preventors or modifiers such as triaryl phosphates, dyes, cetane improvers, auxiliary antioxidants such as 2,6-di-t-butyl-4-methylphenol, rust inhibitors such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the aforedescribed compositions are combined with an ashless dispersant in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Patent No. 1,396,645, British Patent Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0, preferably about 1 to about 10 parts of composition to 1 part ashless dispersant. In still another embodiment of this invention, the inventive additives are combined with Mannich condensation products formed from substituted phenols, aldehydes, polyamines, and substituted pyridines. Such condensation products are described in U.S. Pat. Nos.

3,649,659; 3,558,743; 3,539,633; 3,704,308; and 3,725,277.

The compositions of this invention can be added directly to the fuel to form the fuel compositions of this invention or they can be diluted with a substantially inert, normally liquid organic solvent/diluent such as mineral oil, xylene, or a normally liquid fuel as described above, to form an additive concentrate which is then added to the fuel in sufficient amounts to form the inventive fuel composition described herein. These concentrates generally contain about 10 to 90 percent of the compositions of this invention and can contain in addition any of the above described conventional additives, particularly the aforedescribed ashless dispersants in the aforesaid proportions. The remainder of the concentrate is the solvent/diluent.

Many of the above-mentioned extreme pressure agents and corrosion- oxidation inhibitors also serve as antiwear agents. Zinc dialkylphosphorodithioates are a well known example.

Pour point depressants are a particularly useful type of additive often included in the lubricating oils described herein. The use of such pour point depressants in oil-based compositions to improve low temperature properties is well known in the art. See, for example, page 8 of "Lubricant Additives" by C. V. Smalheer and R. Kennedy Smith (Lezius-Hiles Co. publishers, Cleveland, Ohio, 1967).

Examples of useful pour point depressants are polymethacrylates, polyacrylates; polyacrylamides; condensation products of haloparaffin waxes and aromatic compounds; vinyl carboxylate polymers; and terpolymers of dialkylfumarates, vinylesters of fatty acids and alkylvinylethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference for their relevant disclosures.

Anti-foam agents are used to reduce or prevent the formation of stable foam. Typical anti-foam agents include silicones or organic polymers. Additional antifoam compositions are described in "Foam Control Agents", by Henry T. Kerner (Noyes Data Corporation, 1976), pages 125–162.

The oil-soluble, metal-containing compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain from about 10 to 90% by weight of the oil-soluble, metal-containing compositions of this invention and may contain, in addition, one or more other additives known in the art or described hereinabove. The remainder of the concentrate is the substantially inert normally liquid diluent.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for preparing an overbased composition which comprises reacting (A) a source of an oil soluble sulfonic acid,
(B) a metal containing compound selected from the group consisting of metal oxides, metal hydroxides, metal halides, metal carbonates, metal borates and mixtures thereof and wherein the metal is at least one transition metal,
(C) a boron compound selected from the group consisting of boric acid, boron trioxide, boron halides, boron amides, boron esters, in the presence of
(D) a promoter system wherein the process is conducted at a temperature from about ambient to about the decomposition temperature of any component or product and wherein the ratio range of reactants is expressed by the equation $$\text{Ratio} = \frac{\text{Moles of Boron}}{\text{Eqs of (B)} - \text{Eqs of (A)} - \text{Eqs of acid in (D)} + \text{Eqs of base in (D)}}$$

and is from about 0.2 to about 3.0 wherein (A) additionally comprises a carboxylic acid, a substituted phenol, a phosphorus acid or mixtures thereof.

2. The process according to claim 1 wherein the carboxylic acid is selected from the group consisting of $R(COOH)_n$ wherein n is an integer of at least one and

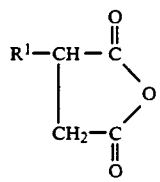

or mixtures thereof with R and $R^1$ being hydrocarbyl-based groups.

3. The process according to claim 2 wherein R is a substantially saturated hydrocarbyl-based group containing from 8 to 100 carbon atoms.

4. The process according to claim 2 wherein $R^1$ is a substantially saturated hydrocarbyl-based group containing from 40 to 750 carbon atoms.

5. The process according to claim 2 wherein n is from 1 to 2.

6. The process according to claim 1 wherein the sulfonic acid is of the formula

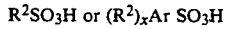

wherein $R^2$ is a hydrocarbyl-based group, x is from 1 to 3 and Ar is an aromatic nucleus.

7. The process according to claim 6 wherein $R^2$ is a substantially saturated hydrocarbyl-based group containing from 8 to 60 carbon atoms.

8. The process according to claim 1 wherein the substituted phenol is of the formula

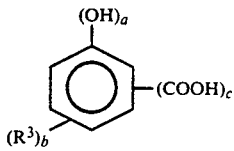

wherein $R^3$ is a substantially saturated hydrocarbyl-based group containing from 15 to 50 carbon atoms; a and b are from 1 to 2 and c is 0 or 1.

9. The process according to claim 1 wherein the substituted phenol is of the formula

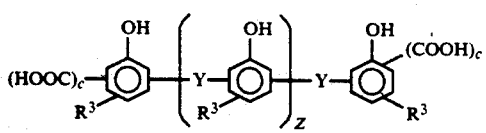

wherein $R^3$ is a substantially saturated hydrocarbyl-based group containing from 6 to 100 carbon atoms, c is 0 or 1, Y is a sulfur linkage or $CH_2$ or mixtures thereof and Z is 0 to 30.

10. The process according to claim 1 wherein the phosphorus acid is prepared from polymers of olefins having 2–30 carbon atoms, said polymer having from 50–100 carbon atoms and said polymer reacted with phosphorus pentasulfide and steam treated.

11. The process according to claim 10 wherein the phosphorus acid is prepared from a polymer of isobutylene.

12. The process according to claim 1 wherein the metal containing compound is a metal oxide selected from the group consisting of zinc oxide, cadmium oxide, and copper oxide.

13. The process according to claim 1 wherein the metal containing compound is a metal hydroxide selected from the group consisting of zinc hydroxide, cadmium hydroxide, and copper hydroxide.

14. The process according to claim 1 wherein the promoter system is at least one member selected from the group consisting of monohydric alcohols up to 20 carbon atoms, dihydric alcohols up to 20 carbon atoms, ammonium hydroxide, water, organic acids up to 8 carbon atoms, nitric acid, hydrochloric acid and sulfuric acid.

15. The process according to claim 1 wherein the promoter system further contains a metal complexing agent.

16. The process according to claim 15 wherein the metal complexing agent is an alkyl salicylaldoxime.

17. The process according to claim 16 wherein the alkyl salicylaldoxime is dodecyl salicylaldoxime.

18. The process according to claim 1 wherein the boron compound is boric acid.

19. The process according to claim 6 wherein the sulfonic acid is a benzene sulfonic acid wherein $R^2$ contains at least 20 carbon atoms; the metal-containing compound is zinc oxide; the boron compound is boric acid; and the promoter system is a mixture comprising ammonium hydroxide, isobutyl alcohol, isoamyl alcohol, water and acetic acid.

20. The process according to claim 6 wherein the sulfonic acid is a benzene sulfonic acid wherein $R^2$ contains at least 20 carbon atoms; the metal-containing compound is copper hydroxide; the boron compound is boric acid; and the promoter system is a mixture comprising acetic acid, isobutyl alcohol, isoamyl alcohol and water.

21. The process according to claim 6 wherein the sulfonic acid is a benzene sulfonic acid wherein $R^2$ contains at least 20 carbon atoms; the metal-containing compound is copper hydroxide; the boron compound is boric acid; and the promoter system is a mixture comprising acetic acid, isobutyl alcohol, isoamyl alcohol, water and a metal complexing agent.

22. The process according to claim 6 wherein the sulfonic acid is a benzene sulfonic acid where $R^2$ contains at least 20 carbon atoms; the metal containing compound is copper hydroxide; the boron compound is boric acid; and the promoter system is a mixture comprising acetic acid, isobutyl alcohol, isoamyl alcohol, water and an alkyl salicylaldoxime.

23. The process according to claim 6 wherein the sulfonic acid is benzene sulfonic acid where $R^2$ contains at least 20 carbon atoms; the metal-containing compound is copper hydroxide; the boron compound is boric acid; and the promoter system is a mixture comprising acetic acid isobutyl alcohol isoamyl alcohol water and dodecyl salicylaldoxime.

24. The process according to claim 1 wherein the ratio range is from 0.5 to about 2.0.

25. The process of claim 1 wherein the oil soluble sulfonic acid is a mixture of a benzene sulfonic acid of the formula $$R^2SO_3H \text{ or } (R^2)_xArSO_3H$$

wherein $R_2$ is a hydrocarbyl-based group containing at least 20 carbon atoms, x is from 1 to 3 and Ar is an aromatic nucleus; and a carboxylic acid of the formula $R^1(CO)_2O$ wherein $R^1$ contains at least 20 carbon atoms; wherein the metal-containing compound is zinc oxide, wherein the boron-containing compound is boric acid; and wherein the promoter system is a mixture comprising ammonium hydroxide, isobutyl alcohol, isoamyl alcohol and acetic acid.

* * * * *